United States Patent
Bruder et al.

(10) Patent No.: US 8,588,493 B2
(45) Date of Patent: Nov. 19, 2013

(54) CT IMAGE RECONSTRUCTION FOR IMPROVING TEMPORAL RESOLUTION IN CARDIO CT

(75) Inventors: Herbert Bruder, Höchstadt (DE); Thomas Flohr, Uehlfeld (DE); Rainer Raupach, Heroldsbach (DE); Karl Stierstorfer, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 573 days.

(21) Appl. No.: 12/849,082

(22) Filed: Aug. 3, 2010

(65) Prior Publication Data
US 2011/0033097 A1    Feb. 10, 2011

(30) Foreign Application Priority Data
Aug. 5, 2009  (DE) .......................... 10 2009 036 232

(51) Int. Cl.
*G06K 9/00*    (2006.01)

(52) U.S. Cl.
USPC ........................................................... 382/131

(58) Field of Classification Search
USPC ........................................................... 382/131
See application file for complete search history.

(56) References Cited

U.S. PATENT DOCUMENTS

| 5,396,528 | A * | 3/1995 | Hu et al. ........................ | 378/14 |
| 7,706,499 | B2 * | 4/2010 | Pack et al. ..................... | 378/9 |
| 2004/0057089 | A1 * | 3/2004 | Voelkl ............................. | 359/1 |
| 2009/0161935 | A1 | 6/2009 | Bruder et al. | |

FOREIGN PATENT DOCUMENTS

DE    102007061935 A1    6/2009

OTHER PUBLICATIONS

Guang-Hong Chen, Jie Tang, Jiang Hsieh, Temporal resolution improvement using PICCS in MDCT cardiac imaging Med. Phys. 36 (6), Jun. 2009; Magazine; 2009; US.
Prior image constrained compressed sensing (PICCS): A method to accurately reconstruct dynamic CT imgages from highly undersampled projection data sets Guang-Hong Chen, Jie Tang, and Shuai Leng Med. Phys. vol. 35, No. 2; Magazine; 2008; US.

* cited by examiner

*Primary Examiner* — Hiep V Nguyen
(74) *Attorney, Agent, or Firm* — Harness, Dickey & Pierce, P.L.C.

(57) ABSTRACT

A method is disclosed for reconstructing image data of a moving examination object from measurement data, wherein the measurement data was captured in the course of a relative rotational movement between a radiation source of a computed tomography system and the examination object. In at least one embodiment of the method, a first image of the examination object is calculated from a complete measurement data record of the measurement data for an image reconstruction and a second image of the examination object is calculated from an incomplete measurement data record of the measurement data for an image reconstruction. Frequency splitting of the first and second images takes place respectively in at least one low-frequency and one higher-frequency component and the image data of the second image is supplemented in the low-frequency component with image data of the low-frequency component of the first image. In a further processing step the second image thus supplemented is improved using the first image, in that errors due to the incompleteness of the measurement data record of the second image are reduced.

15 Claims, 6 Drawing Sheets

CT IMAGE RECONSTRUCTION FOR IMPROVING TEMPORAL RESOLUTION IN CARDIO CT

PRIORITY STATEMENT

The present application hereby claims priority under 35 U.S.C. §119 on German patent application number DE 10 2009 036 232.0 filed Aug. 5, 2009, the entire contents of which are hereby incorporated herein by reference.

FIELD

At least one embodiment of the invention generally relates to a method for reconstructing image data of a moving examination object from measurement data, the measurement data having been captured in the course of a relative rotational movement between a radiation source of a computed tomography system and the examination object.

BACKGROUND

Methods for scanning an examination object using a CT system are generally known. These use for example circular scans, sequential circular scans with advance or spiral scans. During such scans at least one x-ray source and at least one opposing detector are used to record absorption data of the examination object from different recording angles and the absorption data or projections thus collected is/are processed by means of corresponding reconstruction methods to provide sectional images through the examination object.

To reconstruct computed tomography images from x-ray CT data records of a computed tomography device (CT device), i.e. from the captured projections, the standard method currently used is what is known as a filtered back projection or FBP method. Once the data has been captured, what is known as a rebinning step is carried out, in which the data generated with the beam propagated in the manner of a fan from the source is restructured so that it is present as if the detector were struck by x-ray beams arriving at the detector in a parallel manner. The data is then transformed to the frequency domain. Filtering takes place in the frequency domain and the filtered data is then back transformed. The data that has been reorganized and filtered thus is then used for a back projection onto the individual voxels within the volume of interest. However the approximate mode of operation of the conventional FBP methods results in problems with what are known as low-frequency cone beam artifacts and spiral artifacts.

In recent times therefore iterative reconstruction methods have been developed, which can eliminate at least some of the limitations of the FBP methods. With such an iterative reconstruction method initial image data from the projection measurement data is first reconstructed. A convolution back projection method for example can be used to this end. From this initial image data a "projector" or projection operator, which is intended to map the measurement system mathematically as effectively as possible, is used to generate synthetic projection data. The difference in relation to the measurement signals is then back projected using the operator adjoined to the projector and a residual image is thus reconstructed, which is used to update the initial image. The updated image data can in turn be used in a subsequent iteration step with the aid of the projection operator to generate new synthetic projection data, form the difference in relation to the measurement signals from this again and calculate a new residual image, which is again used to improve the image data of the current iteration stage, etc. Such a method allows image data to be reconstructed that has relatively good image sharpness but still has a low level of image noise.

One disadvantage of all calculation methods is that, when the examination object is moving or at least partially moving, motion blur can occur in the image, since during the time of a scanning operation for the data required for an image, a locational offset of the examination object or a part of the examination object may be present, so the measurement data producing an image does not all reflect a spatially identical situation of the examination object. This motion blur problem is particularly prevalent when carrying out cardio CT examinations of a patient, in which the movement of the heart can produce a high level of motion blur in the region of the heart or for examinations in which relatively fast changes in the examination object are to be measured.

The unwanted motion artifacts are reduced by increasing the temporal resolution of the CT recording. There are various procedures for this. On the one hand it is possible to reduce the gantry rotation time. However this soon encounters mechanical limitations, since the centrifugal force acting on the components increases quadratically as the rotation time decreases. On the other hand it is possible in the context of image reconstruction to improve temporal resolution by using in phase, complementary angle data of adjacent cardiac cycles. However the gain depends on the ratio of heart rate to gantry rotation time and cannot easily be influenced. Finally dual emitter CT systems have been developed, in other words CT devices with two x-ray sources and detectors assigned to these. The fact that measurement time is halved due to the presence of two x-ray source/detector systems allows double the temporal resolution. The disadvantage here is that the costs of the duplicated design of the core components, such as the emitter, detector, etc., are considerable.

SUMMARY

In at least one embodiment of the invention, a method is disclosed for reconstructing CT images, wherein it is to be taken into account that a moving examination object is present. In at least one embodiment, a corresponding control and computation unit, a CT system, a computer program and a computer program product are also to be demonstrated.

For at least one embodiment of the inventive method for reconstructing image data of a moving examination object from measurement data, the measurement data has been captured previously in the course of a relative rotational movement between a radiation source of a computed tomography system and the examination object. A first image of the examination object is calculated from a complete measurement data record of the measurement data for image reconstruction purposes. A second image of the examination object is also calculated from an incomplete measurement data record of the measurement data for image reconstruction purposes. There follows frequency splitting of the first and second images respectively into at least one low-frequency and one higher-frequency component. The image data of the second image is supplemented in the low-frequency component with image data of the low-frequency component of the first image. In a further processing step the second image thus supplemented is improved using the first image, in that errors due to the incompleteness of the measurement data record of the second image are reduced.

On the one hand, a complete measurement data record of the captured measurement data is used to reconstruct the first image therefrom. This reconstruction can take place in the manner known per se, e.g. by means of FBP. The completeness of the measurement data record in the case of a measurement in fan beam geometry means that projections are used over a continuous projection angle range of 180° plus the fan opening angle for image reconstruction. After parallel rebinning, in other words the restructuring of the measurement data in parallel beam geometry, the minimum length of the reconstruction interval is therefore 180°.

An incomplete measurement data record of the measurement data is also used to reconstruct the second image therefrom. This incomplete measurement data record therefore contains projections over a continuous projection angle range that is smaller than the abovementioned values of 180° or 180° plus the fan opening angle. The reconstruction of the second image can also take place in the manner known per se, e.g. by way of FBP.

The incomplete measurement data record is preferably a subset of the complete measurement data record. This means that the first and second images map the examination object at the same point in time, the temporal resolution of the first image being lower than that of the second image.

The incompleteness of the measurement data record used means that the second image has artifacts. However the second image has the advantage that less time has elapsed when capturing the measurement data record than with the first image so the motion artifacts are less marked. This is why the second image is processed further so that it can be output as the resulting image with high temporal resolution.

The two images can be displayed in both location space and frequency space, it being possible to switch between the two spaces by way of a multidimensional Fourier transform. In the case of two-dimensional slice images a two-dimensional Fourier transform has to take place for this purpose and in the case of three-dimensional volume images a three-dimensional Fourier transform.

In frequency space frequency splitting is carried out for both the first and second images. A distinction is made here between at least two domains: one domain with low frequencies and one domain with the other frequencies. The domain with low frequencies corresponds in the case of two-dimensional images to a surface in frequency space that contains the zero point and correspondingly in three-dimensional images to a volume in frequency space that contains the zero point. Frequency splitting is preferably identical for the first and second images.

The low-frequency domain of the second image is modified. To this end image data of the low-frequency domain of the first image is added to this domain. With regard to an individual data item this means that at a certain point in frequency space of the first image the respective image value is allocated the corresponding image value of the identical point of the second image. This preferably takes place for all points within the low-frequency component of the image data of the second image. It is however also possible just to allocate pixel values of the first image to some points of the second image. The concept of supplementing not only covers the allocating of image values of the first image as described above but also an offsetting of pixel values of the first image with pixel values of the second image.

The modification in the low-frequency domain already causes the artifacts of the second image to be reduced to some extent. Since however there is no modification of the image data in the higher-frequency domain, image errors are not completely eliminated. The second image is therefore improved further, the first image also being used in this process. This improvement causes at least some of the errors due to the incompleteness of the measurement data record of the second image to be reduced. This can be done by aligning the supplemented second image with the first image, at least in so far as the first image is not affected by artifacts which are present in the second image.

In one development of at least one embodiment of the invention the incompleteness of the measurement data record in the case of the second image means that incomplete image data is present in frequency space and supplementing the image data only partially completes this incomplete image data. Looking at frequency space therefore there are not image data values for all the points in the second image. This does not affect the first image, as a complete measurement data record was used for this. The incomplete presence of image data values of the second image is partially remedied by supplementing it with image data of the first image. In particular it is advantageous if the image data of the second image is fully completed in the low-frequency domain. Completion—either full or partial—also preferably does not take place in the higher-frequency domain.

In one development of the invention frequency splitting is embodied so that the image data of the first image contains few motion artifacts in the low-frequency component. In some circumstances this requires a complex analysis of the motion artifacts and a corresponding development of a suitable function, which can be used for frequency splitting.

According to one development of at least one embodiment of the invention, the further processing step takes place iteratively. In other words, the supplemented second image is improved in a number of individual steps, with the first image being used in each individual step and the second image being processed in the same manner in each individual step, with the second image output by the last individual step being used in each instance as the basis for processing. In the first individual step the supplemented second image is used as the first estimated image for the iteration.

The further processing step preferably brings about an alignment of the supplemented second image with the first image. This allows artifacts, which are still contained in the second image despite the supplementing carried out in the low-frequency domain and are not contained in the first image due to the completeness of the measurement data record, to be reduced.

In one embodiment of the invention, the further processing step comprises the minimization of a function that contains both image data of the supplemented second image and also image data of the first image. Minimization is recommended in particular in conjunction with the iterative procedure. During minimization a target function can be predetermined, which predetermines characteristics of the second image to be achieved or avoided. The target function can be minimized for example with a gradient method relating to a selected standard.

In particular the function can contain two summands, one summand relating to a difference between the supplemented second image and the first image and the second summand relating to the supplemented second image. For example the first-mentioned summand can comprise an edge image of the difference between the supplemented second image and the first image and the second-mentioned summand an edge image of the supplemented second image. An edge image of an image is obtained when the image is subjected to an operation, e.g. a high pass, which emphasizes the edges rather than the other image components.

According to one development of at least one embodiment of the invention, a second further processing step after the further processing step can comprise an iterative image reconstruction of the improved second image for tailoring to the incomplete measurement data record. Methods known per se can be used for this. It is advantageous before the second further processing step is carried out to verify whether the quality of the second image is adequate after the completed further processing step, in which instance there is no need to carry out the second further processing step.

It is possible for the further processing step to follow the second further processing step again. This allows the second further processing step and the further processing step to be repeated iteratively.

The inventive control and computation unit serves to reconstruct image data of an examination object from measurement data of a CT system. In at least one embodiment, it comprises a program storage unit for storing program code, with program code—in some instances as well as other things—being present therein, which is suitable for executing a method of the type described above. The inventive CT system of at least one embodiment comprises such a control and computation unit. It may also contain other components that are required for example to capture measurement data.

The inventive computer program of at least one embodiment has program code segments or modules, which are suitable for carrying out the method of the type described above, when the computer program is executed on a computer.

The inventive computer program product of at least one embodiment comprises program code segments or modules stored on a computer-readable data medium, which are suitable for carrying out the method of the type mentioned above, when the computer program is executed on a computer.

BRIEF DESCRIPTION OF THE DRAWINGS

The invention is described in more detail below with reference to an example embodiment. In the drawings.

DETAILED DESCRIPTION OF THE EXAMPLE EMBODIMENTS

Figure 1:
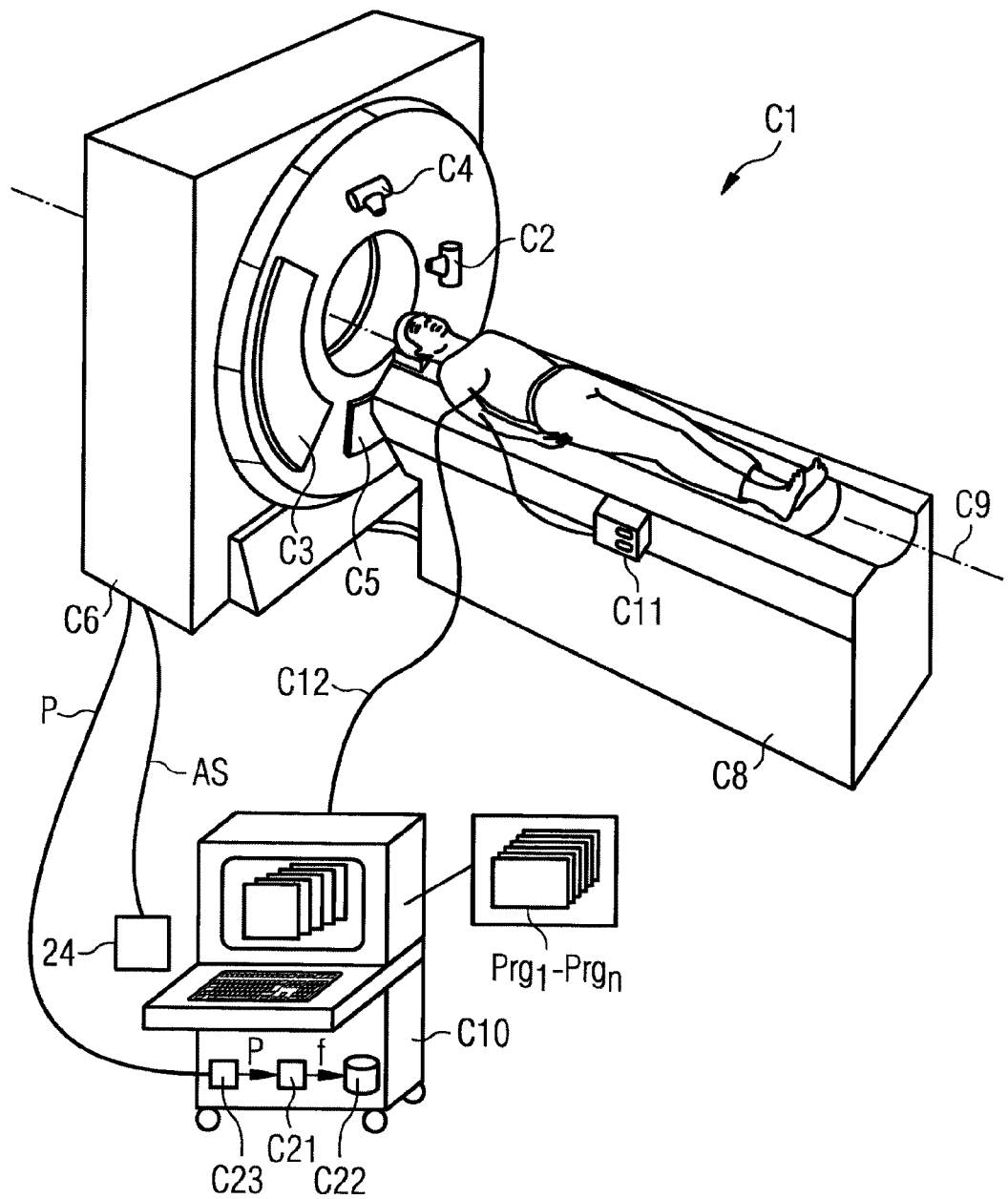
FIG. 1: shows a first schematic diagram of an example embodiment of a computed tomography system having an image reconstruction component.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

FIG. 1 first shows a schematic diagram of a first computed tomography system C1 having an image reconstruction facility C21. In the gantry housing C6 is a closed gantry (not shown here), on which a first x-ray tube C2 and an opposing detector C3 are disposed. Optionally disposed in the CT system illustrated here is a second x-ray tube C4 with an opposing detector C5, the additionally available emitter/detector combination allowing a higher temporal resolution to be achieved or the use of different x-ray energy spectra in the emitter/detector system also allowing dual energy examinations to be carried out.

The CT system C1 also has a patient couch C8, on which a patient can be moved into the measurement field during the examination along a system axis C9, also referred to as the z-axis, in which process the scan itself can take place both as a purely circular scan without the patient being advanced exclusively in the examination region of interest. The x-ray source C2 and/or C4 rotates around the patient here. The detector C3 and/or C5 here moves along in a parallel manner opposite the x-ray source C2 and/or C4, to capture projection measurement data which is then used to reconstruct sectional images. As an alternative to a sequential scan, in which the patient is moved through the examination field between the individual scans gradually, there is of course also the option of a spiral scan, in which the patient is moved continuously along the system axis C9 through the examination field between the x-ray tube C2 and/or C4 and the detector C3 and/or C5 during the rotational scan with x-ray radiation. The movement of the patient along the axis C9 and the simultaneous rotation of the x-ray source C2 and/or C4 during a spiral scan produces a helical path for the x-ray source C2 and/or C4 relative to the patient during measurement. This path can also be achieved by moving the gantry along the axis C9 while the patient remains stationary.

The CT system 10 is controlled by a control and computation unit C10 with computer program code $Prg_1$ to $Prg_n$, present in a storage unit. Acquisition control signals AS can be transmitted from the control and computation unit C10 by way of a control interface 24, to activate the CT system C1 according to certain measurement protocols.

The projection measurement data p acquired by the detector C3 and/or C5 (also referred to below as raw data) is transferred by way of a raw data interface C23 to the control and computation unit C10. This raw data p is then further processed in an image reconstruction component C21, optionally after appropriate preprocessing. The image reconstruction component C21 in this example embodiment is implemented on a processor in the control and computation unit C10 in the form of software, e.g. in the form of one or more of the computer program codes $Prg_1$ to $Prg_n$. The image data f reconstructed by the image reconstruction component C21 is then stored in a storage unit C22 of the control and computation unit C10 and/or output in the usual manner on the screen of the control and computation unit C10. It can also be fed by way of an interface (not shown in FIG. 1) into a network linked to the computed tomography system C1, for example a radiological information system (RIS), and stored in a mass storage unit that is accessible there or output as images.

The control and computation unit C10 can also execute the function of an ECG, a line C12 being used to pick up the ECG potentials between the patient and the control and computation unit C10. The CT system C1 shown in FIG. 1 also has a contrast agent injector C11, by way of which contrast agent can also be injected into the blood stream of the patient, so that the vessels of the patient, in particular the ventricles of the beating heart, can be displayed more clearly. It is also possible to carry out perfusion measurements, for which the proposed method is likewise suitable.

Figure 2:
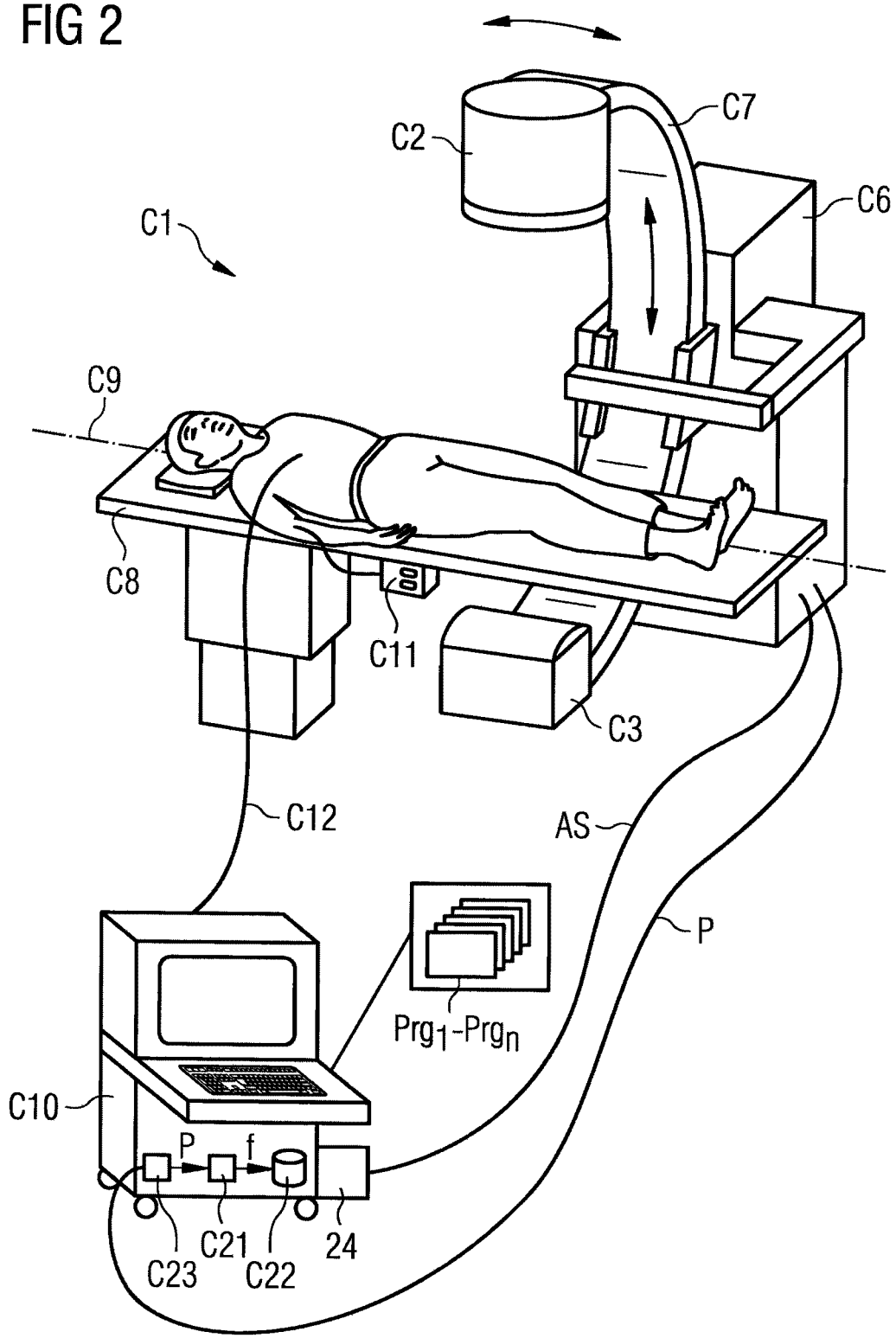
FIG. 2: shows a second schematic diagram of an example embodiment of a computed tomography system having an image reconstruction component.

FIG. 2 shows a C-arm system, with which in contrast to the CT system in FIG. 1 the housing C6 supports the C-arm C7, to which the x-ray tube C2 is secured on one side and the opposing detector C3 on the other side. The C-arm C7 is likewise pivoted about a system axis C9 for scanning purposes, so that a scan can take place from a plurality of scan angles and corresponding projection data p can be determined from a plurality of projection angles. Like the CT system in FIG. 1 the C-arm system C1 in FIG. 2 also has a control and computation unit C10 of the type described in relation to FIG. 1.

Embodiments of the invention can be applied in both the systems shown in FIGS. 1 and 2. They can also be used in principle for other CT systems, e.g. for CT systems with a detector forming a complete ring.

In so far as body parts of the patient are to be recorded, which do not move or remain still, no significant problems arise when recording the projections and carrying out the subsequent image reconstruction. In contrast this is critical for moving examination objects. The situation where a CT recording of a moving examination object is to be carried out is considered in the following.

Figure 3:
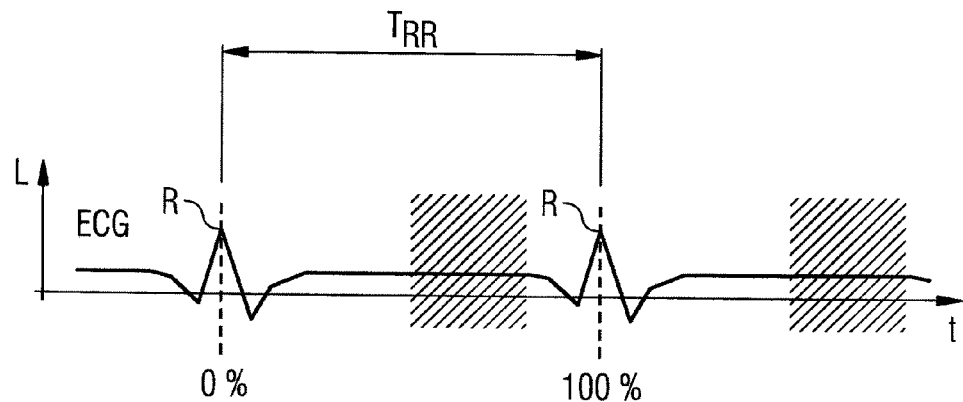
FIG. 3: shows a cardiac cycle.

One example of a periodically moving examination object is the human heart. The human heart is known to execute an essentially periodic movement. The periodic movement here consists of an alternating sequence of a rest or slack phase and a movement or beat phase. The rest phase generally lasts between 500 and 800 ms, the beat phase between 200 and 250 ms. This can be seen in FIG. 3, where the level L of the ECG signal (shown as ECG) of a patient is shown over time t. The ECG signal illustrates the periodic movement of the heart of the patient, the start of a cardiac cycle being determined in each instance by an R-wave R and the duration of the respective cardiac cycle being determined by the RR-interval $T_{RR}$, i.e. the interval between the R-wave R initiating the respective cardiac cycle and the R-wave R initiating the following cardiac cycle. A cardiac phase starts with an R-wave R at 0% and ends with the next R-wave R at 100%. It is possible to convert between the dimension of time and cardiac phase at any time. The ECG data can be used for this, it being possible to conclude from this at any time which cardiac phase is currently present. The rest phase of the heart, i.e. the phase of minimal heart movement, is shown hatched in each instance.

When carrying out cardiac imaging by way of CT the cardiac phase in which the data is recorded is vital for good image quality. Attempts are made for image reconstruction to use data captured during a cardiac phase with little or minimal heart movement.

In addition to the requirements relating to the quality of CT images which are also demanded of unmoving examination objects, the aim with cardiac recordings is to achieve high temporal resolution of the images. Temporal resolution here is inversely proportional to the time required to capture the projections. The more time that elapses while the data is being captured, the more the heart moves during this measurement period. This movement produces unwanted motion artifacts in the CT images. The information provided by the CT image is drastically reduced as a result.

Figure 4:
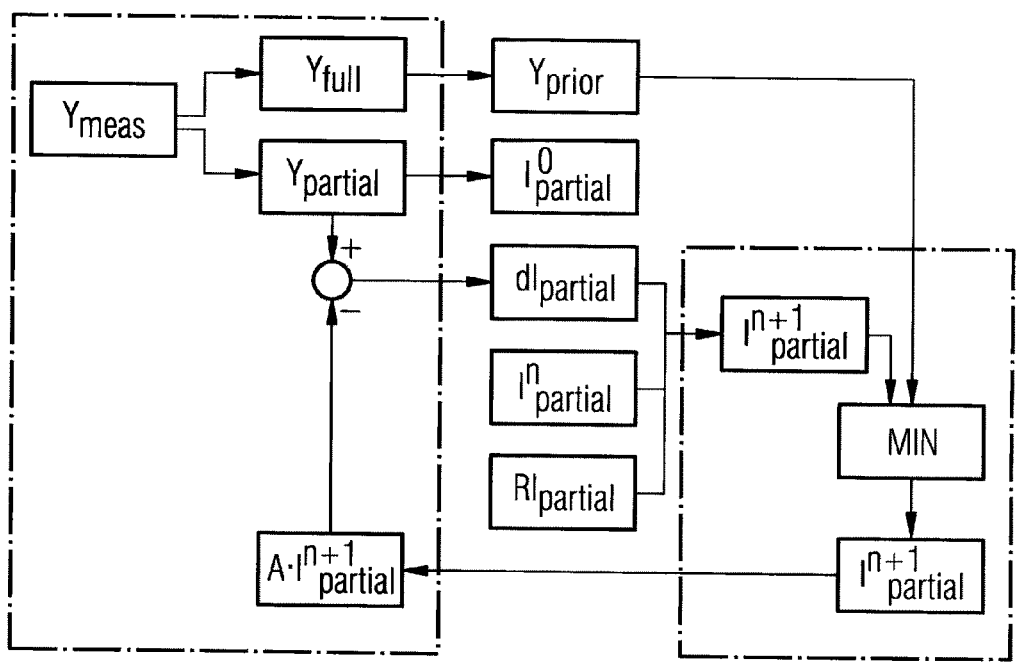
FIG. 4: shows a first flow diagram to illustrate a method sequence.

FIG. 4 shows a flow diagram of the method described below. The measurement data $Y_{meas}$ is captured first. The data can be captured here with or without the examination object being advanced relative to the x-ray source. A first part $Y_{full}$ of the measurement data $Y_{meas}$ is isolated here. This consists of projection data from an angle range required for a regular image calculation. In the case of measurements with parallel beam geometry this is an angle range of 180°, in the case of measurements with fan beam geometry 180° plus the fan angle. A first image $I_{prior}$ is reconstructed from the part $Y_{full}$ of the measurement data and is referred to in the following as the prior image $I_{prior}$. The prior image has the above-mentioned disadvantage that it contains motion artifacts due to the heart movement.

A second part $Y_{partial}$ of the measurement data $Y_{meas}$ is also isolated. This data $Y_{partial}$ is a subset of the first part $Y_{full}$. The measurement data $Y_{partial}$ therefore does not contain all the projections required for a regular image reconstruction, only measurement data from a smaller continuous projection angle range. For example the measurement data $Y_{partial}$ can originate from a projection angle range of 120°.

A second image $I^0_{partial}$ is reconstructed from the measurement data $Y_{partial}$ and is referred to in the following as the partial image. In contrast to the prior image $I_{prior}$ this partial image $I^0_{partial}$ has the advantage that it contains fewer motion artifacts. The shorter measurement time required to capture the projections $Y_{partial}$ means that the temporal resolution of the partial image $I^0_{partial}$ is better than that of the prior image $I_{prior}$. However the partial image $I^0_{partial}$ does contain artifacts due to the incompleteness of the measurement data $Y_{partial}$. These are referred to as "limited view angle" artifacts. They manifest themselves in particular through visible distortions within the image in directions for which no projections are available for image reconstruction.

Figure 5A:
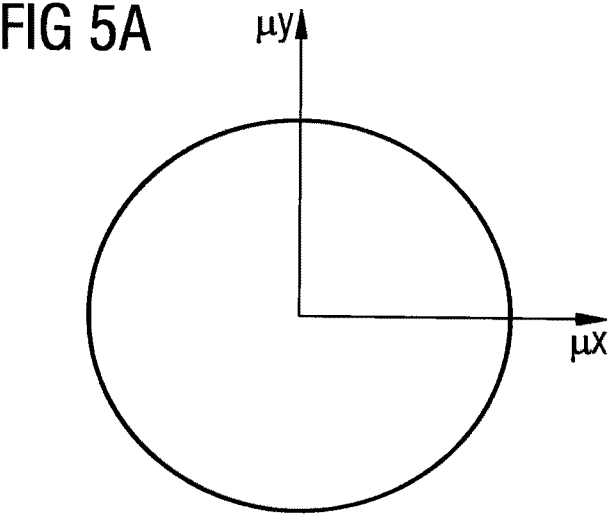
FIG. 5: shows the presence of image data in frequency space.
Figure 5B:
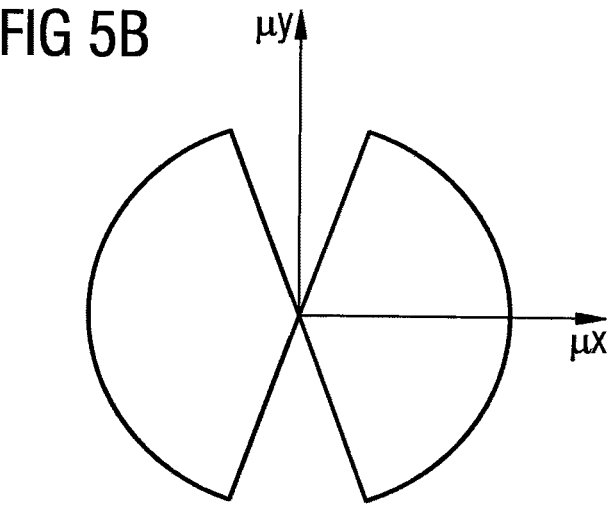

The differing presence of image data within the two image data records $I_{prior}$ and $I^0_{partial}$ is illustrated in FIGS. 5A and 5B. These are frequency space diagrams, i.e. the image data $I_{prior}$ and $I^0_{partial}$ has been transformed by way of a Fourier transform from location space to frequency space. The two frequencies $\mu_x$ and $\mu_y$ are plotted on both axes. The diagrams show the frequencies for which image data is present:

FIG. 5A corresponds to the prior image $I_{prior}$. It can be seen that image data is present for all frequencies.

FIG. 5B in contrast corresponds to the partial image $I^0_{partial}$. Because of the incomplete angle scan of the measurement data $Y_{partial}$ every missing projection according to the Fourier slice theorem produces missing image data in the corresponding direction in the Fourier spectrum of the image. This missing image data corresponds to cones cut out of the complete data record. Therefore image data is missing in particular at high-figure values of the frequency $\mu_x$.

Because of the better temporal resolution the partial image $I^0_{partial}$ is to be used as the basis for the image to be output as the result. However since this has "limited view angle" artifacts, it is improved beforehand in this respect. This improvement takes place in two stages, with the prior image $I^0_{prior}$ being used in the second stage. The first and second stages are applied a number of times one after the other; an iterative procedure is thus applied. The partial image of the nth iteration is referred to as $I^n_{partial}$. In the first iteration therefore the partial image $I^0_{partial}$ is processed to obtain the partial image $I^1_{partial}$.

The first stage is a conventional iterative image reconstruction. Therefore methods known per se, such as ART for example, can be applied for the iterative reconstruction. In this process the partial image $I^n_{partial}$ is aligned iteratively with the measurement data $Y_{partial}$, i.e. $A \cdot I^n_{partial} = Y_{partial}$ should apply. A here is a system matrix, which simulates the measurement process. The application of A to an image therefore corresponds to a forward projection, so the result of this calculation is projection data.

In the iterative image reconstruction the variables $dI_{partial}$, $I^n_{partial}$ and $RI_{partial}$ are used in the context of each partial iteration step.

$dI_{partial}$ is the difference between the measurement data $Y_{partial}$ and the projection data calculated using the partial image $I^n_{partial}$ of the last iteration over $A \cdot I^n_{partial}$. In the first iteration therefore to determine $dI_{partial}$ the result of $A \cdot I^0_{partial}$ is subtracted from the measurement data $Y_{partial}$.

$RI_{partial}$ is an image obtained by applying an operator R to the image of the last iteration. R is an image filter for noise reduction.

A new image is calculated by adding the three variables $dI_{partial}$, $I^n_{partial}$ and $RI_{partial}$. In the first iteration therefore $dI_{partial} = Y_{partial} - A \cdot I^0_{partial}$ and $R \cdot I^0_{partial}$ and $I^0_{partial}$ are added to obtain the new image $I^1_{partial}$.

After the end of the iterative image reconstruction a reworked partial image $I^{n+1}_{partial}$ is present. This is now used in the second stage. In the second stage MIN the cost function $$[\alpha \cdot |\psi(I_{partial} - I_{Prior})|_{lp} + (1-\alpha) \cdot |\psi(I_{partial})|_{lp}]$$

is minimized. Here $\Psi$ designates an edge image operator corresponding to a high pass, $\alpha$ a parameter between 0 and 1, which represents the relative weighting between the two terms, and $l_p$ the p-norm of a vector $$|\vec{x}|_{lp} = (|x_1|^p + \ldots + |x_N|^p)^{1/p}.$$

The difference $I_{partial} - I_{Prior}$ comprises the differences between the partial image $I_{partial}$ of the current iteration and the prior image $I_{prior}$. In the first iteration the difference $I^1_{partial} - I_{Prior}$ is thus formed. The related minimization is advantageous for two reasons: on the one hand the partial image $I_{partial}$ contains the "limited view angle" artifacts, which make up part of the difference in respect of the prior image $I_{prior}$. This differential term is used for the partial image $I_{partial}$ to be calculated in the context of the minimization MIN to obtain the edges contained in the prior image $I_{prior}$ but missing from the partial image $I_{partial}$ due to the incomplete partial data.

On the other hand the prior image $I_{prior}$ contains motion artifacts which also make up part of the difference in respect of the partial image $I_{partial}$ and are to be eliminated. In the artial context of the minimization step MIN attempts are therefore made to increase the similarity of the prior image $I_{prior}$ to the partial image $I_{partial}$, by on the one hand reducing the "limited view angle" artifacts of the partial image $I_{partial}$, without on the other hand carrying over the motion artifacts of the prior image $I_{prior}$ into the partial image $I_{partial}$.

Minimization of the second term of the cost function is based on the consideration that both the motion artifacts and the "limited view angle" artifacts manifest themselves in particular at high frequencies. An attempt should therefore be made to eliminate these high-frequency artifacts.

Minimization MIN of the cost function takes place by way of the steepest descent method. The procedure is iterative here too. The following equation is used:

$$I^{k+1}_{partial} = I^k_{partial} - \gamma \cdot \text{grad}(Z)$$

Here Z is the target function to be minimized, grad(Z) is the derivation of the target function in relation to the partial image $I^k_{partial}$, and $\gamma$ is a parameter. Since the target function contains the prior image $I_{prior}$ in the manner described above, minimization can cause information of the prior image $I_{prior}$, which is missing from the partial image $I_{partial}$ and does not relate to updating, to be transferred to the partial image $I_{partial}$ to be calculated in the context of minimization MIN.

The minimization step MIN processes the partial image $I^{n+1}_{partial}$, which was the result of the first stage, and outputs it as a new partial image $I'^{n+1}_{partial}$. This new partial image $I'^{n+1}_{partial}$ is in turn subjected to the first stage of the conventional iterative image reconstruction.

For a more precise description of the procedure, see G. Chen, J. Tang, J. Hsieh: Temporal resolution improvement using PICCS in MDCT cardiac imaging, Med. Phys. 36(6), June 2009, pp. 2130-2135, the entire contents of which are hereby incorporated herein by reference.

In the first stage, i.e. during the iterative tailoring of the partial image $I^n_{partial}$ to the measurement data $Y_{partial}$, complex projection and back projection operations are required in each iteration step. This takes up a great deal of time and computation capacity. The missing data within the measurement data $Y_{partial}$ means that a large number of iterations are required; it is even possible that there will be no convergence.

Figure 6:
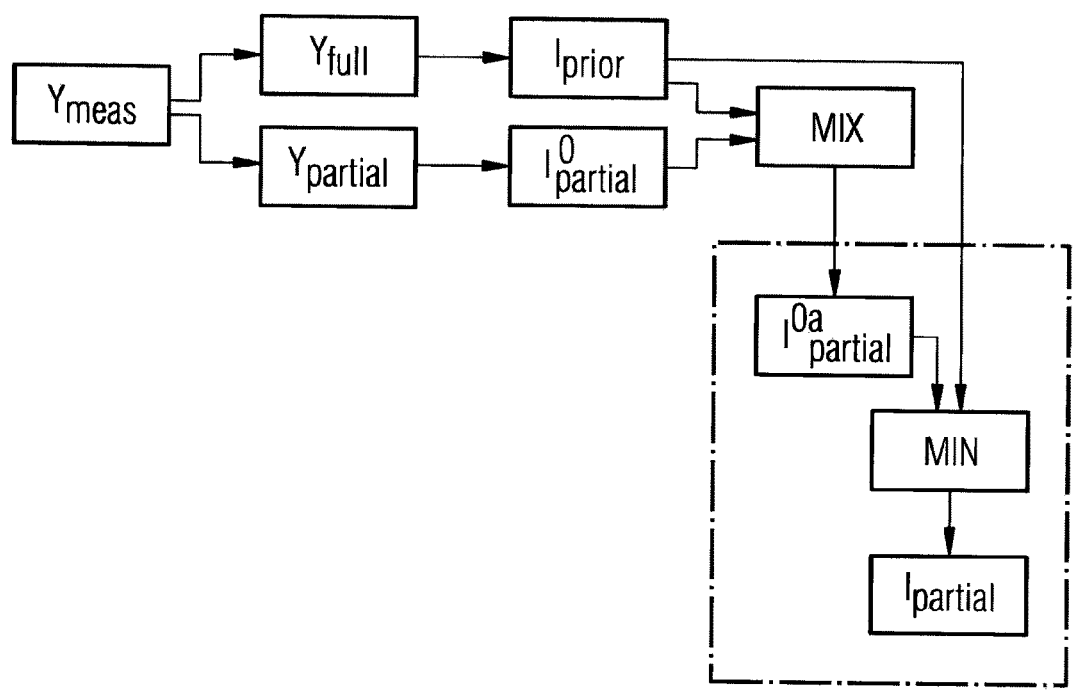
FIG. 6: shows a second flow diagram to illustrate a method sequence.

It is demonstrated in the following how the method described with reference to FIG. 4 can be considerably accelerated. This can be achieved by calculating the first partial image $I^0_{partial}$ differently. This procedure is illustrated using the flow diagram in FIG. 6. As already described in FIG. 4, the prior image $I_{prior}$ and/or the partial image $I^0_{partial}$ is/are calculated from the measurement data $Y_{full}$ and $Y_{partial}$. Before the partial image $I^0_{partial}$ is further improved according to the measures described in relation to FIG. 4, an improved partial image $I^{0a}_{partial}$ is first calculated from the original partial image $I^0_{partial}$ in step MIX.

To this end both the prior image $I_{prior}$ and the partial image $I^0_{partial}$ are moved into the Fourier diagram, i.e. by Fourier transform into frequency space. The presence of image data in frequency space is shown in FIG. 5A for the prior image $I_{prior}$ and in FIG. 5B for the partial image $I^0_{partial}$.

Figure 7:
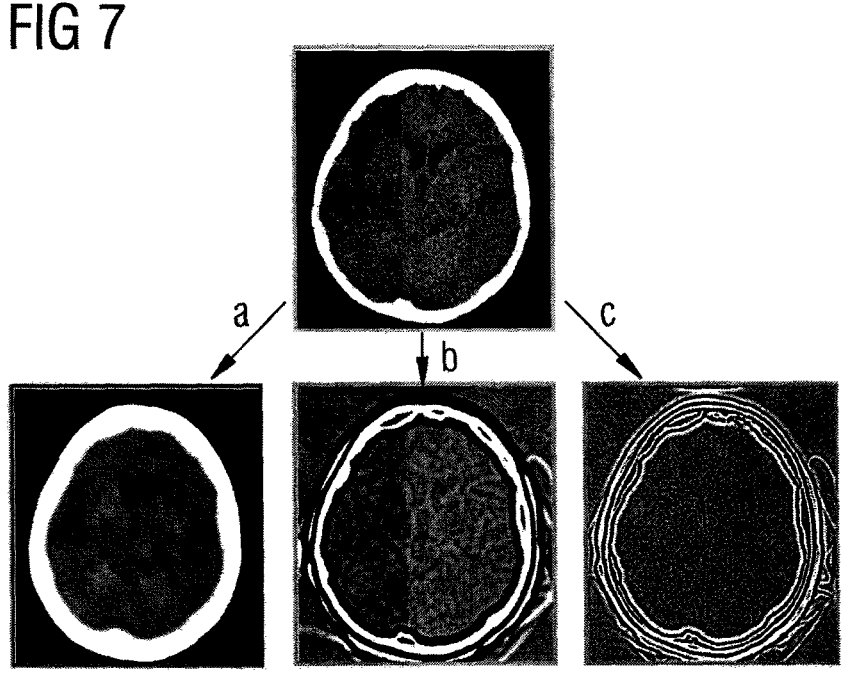
FIG. 7: shows a frequency band decomposition of a CT image.
Figure 7:
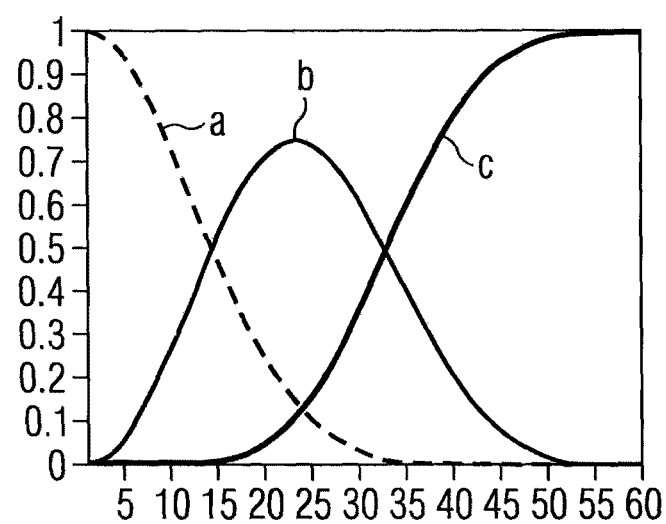

The spectrum of frequency space is now broken down into frequency bands. FIG. 7 shows an example of a frequency band decomposition of a CT image. In this example the frequency spectrum is broken down into three frequency bands. The filter functions a, b, c to be applied in frequency space are shown top left—in one dimension for simplicity. The low-frequency band corresponds to the application of the filter function a. The contrast information of the original image is contained in the image containing these frequencies. The high-frequency band corresponds to the application of the filter function c. The edge information of the original image is contained in the image containing these frequencies.

Figure 5C:
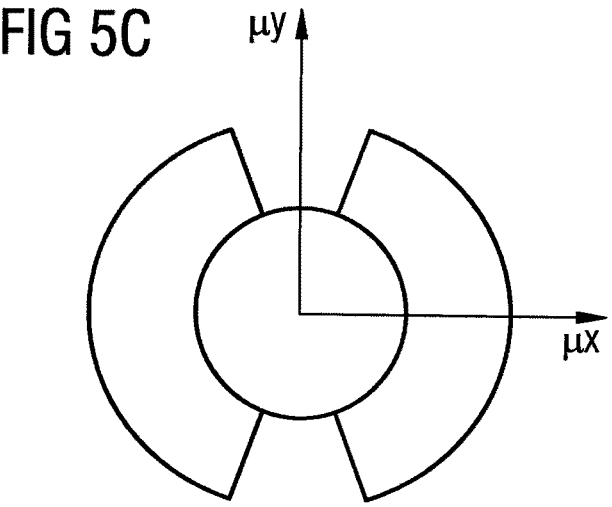

For the purpose of obtaining the partial image $I^{0a}_{partial}$ it is sufficient just to apply two filter functions, the first filter function corresponding to a low-frequency band and the other filter function corresponding to the remaining frequencies. The low-frequency part of the partial image $I^0_{partial}$ is replaced by the low-frequency part of the prior image $I_{prior}$. This is illustrated in FIG. 5C: within the circle, which is located in the center of the diagram at low frequencies, the image data of the partial image $I^0_{partial}$ is replaced by the image data of the prior image $I_{prior}$. This corresponds to the partial filling of the cone-shaped gaps in FIG. 5B. In the domains that are both outside the gaps in FIG. 5B and within the circle in FIG. 5C the image data of the two images $I^0_{partial}$ and $I_{prior}$ corresponds; It is therefore irrelevant whether the data of the partial image $I^0_{partial}$ in this domain is replaced or remains unchanged.

A back transformation of the image data according to FIG. 5C from the frequency to the location domain supplies the required partial image $I^{0a}_{partial}$. This is improved compared with the original partial image $I^0_{partial}$, since artifacts of the original partial image $I^0_{partial}$ have been reduced. This is based on the completion of the frequency content of the partial image $I^0_{partial}$ in the low-frequency domain. This is based on the recognition that the motion artifacts of the prior image $I_{prior}$ mainly manifest themselves in the higher-frequency components of the prior image $I_{prior}$. It is therefore not detrimental with regard to the motion artifacts to improve the low-frequency image component of the partial image $I^0_{partial}$ using the prior image $I_{prior}$ in respect of the incomplete presence of image data in frequency space. Conversely the good temporal resolution of the partial image $I^0_{partial}$ is barely influenced by the modification in the low-frequency domain, since the temporal resolution is contained in the higher frequencies.

Until now the image data of the prior image $I_{prior}$ missing from the low-frequency part has been taken into account in step MIX. To eliminate the artifacts that result due to the missing image data in the higher-frequency domain, the partial image $I^0_{partial}$ is treated with further processing as described in relation to FIG. 4. This starts with the minimization MIN (this corresponds to the second stage described in relation to FIG. 4). It is possible to output the partial image $I_{partial}$ obtained due to minimization MIN as the resulting image. There is then no need for iterative tailoring (this corresponds to the first stage described in relation to FIG. 4). This accelerates the method considerably.

It is however also possible to carry out the iterative tailoring to the measurement data $Y_{partial}$ described as the first stage in FIG. 4 after carrying out the minimization MIN. Minimization MIN can optionally be carried out again after this, etc. Whether these steps are necessary and/or how many such steps are necessary is a function in particular of the quality of the replacement of the low-frequency data. It is particularly important here to use a suitable frequency filter, in order to select in frequency space those components of the partial image $I^0_{partial}$ that are to be replaced by the image data of the prior image $I_{prior}$.

The extent of the achieved improvement of the temporal resolution of the partial image $I_{partial}$ compared with the prior image $I_{prior}$ is a function of the relationship of the measurement ranges $Y_{full}$ and $Y_{partial}$. If the measurement data $Y_{partial}$ originates from a projection angle range of for example 90°, while the measurement data $Y_{full}$—assuming parallel beam geometry—originates from a projection angle range of 180°, the temporal resolution is doubled.

The invention was described above with reference to an example embodiment. It goes without saying that numerous changes and modifications are possible without departing from the scope of the invention. It should be mentioned in particular that the invention can be used both for CT systems having one x-ray source and for CT systems having two or more x-ray sources.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, computer readable medium and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable medium and is adapted to perform any one of the aforementioned methods when run on a computer device (a device including a processor). Thus, the storage medium or computer readable medium, is adapted to store information and is adapted to interact with a data processing facility or computer device to execute the program of any of the above mentioned embodiments and/or to perform the method of any of the above mentioned embodiments.

The computer readable medium or storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for reconstructing image data of a moving examination object from measurement data, wherein the measurement data has been captured in a course of a relative rotational movement between a radiation source of a computed tomography system and the examination object, the method comprising:
    calculating a first image of the examination object from a complete measurement data record of the measurement data for an image reconstruction and a second image of the examination object from an incomplete measurement data record of the measurement data for an image reconstruction;
    frequency splitting the first and second images, respectively, in at least one low-frequency component and one higher-frequency component; and
    supplementing image data of the second image, in the low-frequency component, with image data of the low-frequency component of the first image, wherein in a further processing the supplemented second image is improved using the first image such that errors due to the incompleteness of the measurement data record of the second image are reduced.

2. The method as claimed in claim 1, wherein the incomplete image data is present in a frequency space due to the incompleteness of the measurement data record in the second image, and
    the incomplete image data is only partially completed by supplementing the image data.

3. The method as claimed in claim 1, wherein the frequency splitting is embodied so that the image data of the first image contains few motion artifacts in the low-frequency component.

4. The method as claimed in claim 1, wherein the incomplete measurement data record is a subset of the complete measurement data record.

5. The method as claimed in claim 1, wherein the further processing takes place iteratively.

6. The method as claimed in claim 1, wherein the further processing brings about an alignment of the supplemented second image with the first image.

7. The method as claimed in claim 1, wherein the further processing comprises a minimization of a function containing both image data of the supplemented second image and the image data of the first image.

8. The method as claimed in claim 7, wherein the function contains two summands, one summand relating to a difference between the supplemented second image and the first image and a second summand relating to the supplemented second image.

9. The method as claimed in claim 1, wherein an iterative image reconstruction of the improved second image for tailoring to the incomplete measurement data record takes place as a second further processing after the further processing.

10. The method as claimed in claim 9, wherein the further processing again follows the second further processing.

11. The method as claimed in claim 10, wherein the second further processing and the further processing are repeated iteratively.

12. A control and computation unit for reconstructing image data of an examination object from measurement data of a CT system, configured to:
    calculate a first image of the examination object from a complete measurement data record of the measurement data for an image reconstruction and a second image of the examination object from an incomplete measurement data record of the measurement data for an image reconstruction;

frequency split the first and second images, respectively, in at least one low-frequency component and one higher-frequency component; and supplement image data of the second image, in the low-frequency component, with image data of the low-frequency component of the first image, wherein in a further processing the supplemented second image is improved using the first image in that errors due to the incompleteness of the measurement data record of the second image are reduced.

13. A CT system comprising:

a control and computation unit configured to, calculate a first image of the examination object from a complete measurement data record of the measurement data for an image reconstruction and a second image of the examination object from an incomplete measurement data record of the measurement data for an image reconstruction;

frequency split the first and second images, respectively, in at least one low-frequency component and one higher-frequency component; and supplement image data of the second image, in the low-frequency component, with image data of the low-frequency component of the first image, wherein in a further processing the supplemented second image is improved using the first image in that errors due to the incompleteness of the measurement data record of the second image are reduced.

14. A non-transitory computer readable medium including a computer program product, the computer program product comprising instructions, which when executed by a processor, causes the processor to perform functions including:

calculating a first image of the examination object from a complete measurement data record of the measurement data for an image reconstruction and a second image of the examination object from an incomplete measurement data record of the measurement data for an image reconstruction;

frequency splitting the first and second images, respectively, in at least one low-frequency component and one higher-frequency component; and supplementing image data of the second image, in the low-frequency component, with image data of the low-frequency component of the first image, wherein in a further processing the supplemented second image is improved using the first image in that errors due to the incompleteness of the measurement data record of the second image are reduced.

15. The method as claimed in claim 2, wherein the frequency splitting is embodied so that the image data of the first image contains few motion artifacts in the low-frequency component.

* * * * *